United States Patent
Rowe et al.

(10) Patent No.: US 12,232,762 B2
(45) Date of Patent: Feb. 25, 2025

(54) ATHERECTOMY DEVICES INCLUDING A PLURALITY OF DISTAL CUTTING FEATURES

(71) Applicant: PHILIPS IMAGE GUIDED THERAPY CORPORATION, San Diego, CA (US)

(72) Inventors: Douglas Rowe, San Jose, CA (US); Paul Q Escudero, Redwood City, CA (US); August Christopher Pombo, Sacramento, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 452 days.

(21) Appl. No.: 17/619,586

(22) PCT Filed: Jun. 11, 2020

(86) PCT No.: PCT/EP2020/066184
§ 371 (c)(1),
(2) Date: Dec. 16, 2021

(87) PCT Pub. No.: WO2020/254181
PCT Pub. Date: Dec. 24, 2020

(65) Prior Publication Data
US 2022/0296270 A1  Sep. 22, 2022

Related U.S. Application Data

(60) Provisional application No. 62/863,061, filed on Jun. 18, 2019.

(51) Int. Cl.
*A61B 17/3207* (2006.01)
*A61B 17/00* (2006.01)

(52) U.S. Cl.
CPC ..... *A61B 17/320758* (2013.01); *A61B 2017/003* (2013.01); *A61B 2017/00469* (2013.01); *A61B 2017/320775* (2013.01)

(58) Field of Classification Search
CPC ........... A61B 17/320758; A61B 2017/320775
See application file for complete search history.

(56) References Cited

U.S. PATENT DOCUMENTS

| 4,790,813 A | 12/1988 | Kensey |
| 2002/0143350 A1 | 10/2002 | Heitzmann |

(Continued)

FOREIGN PATENT DOCUMENTS

| EP | 3258863 | 12/2017 |
| WO | 2015/017114 | 2/2015 |

OTHER PUBLICATIONS

International Search Report and Written Opinion Dated Dec. 24, 2020, For International Application No. PCT/EP2020/066184 Filed Jun. 11, 2020.

*Primary Examiner* — Tuan V Nguyen

(57) ABSTRACT

An atherectomy device including a handle configured to be manipulated by a user. The device further includes a catheter comprising an outer sheath and a drive shaft carried within and rotatable relative to the outer sheath. A cutter assembly is coupled to and extends distally relative to the outer sheath. The cutter assembly includes a housing coupled to and extending distally from the outer sheath. A proximal cutting element is rotatably carried by the housing, and the proximal cutting element is coupled to and extends distally from the drive shaft. The proximal cutting element includes a cutting stem having at least one cutting feature and at least one cutting blade coupled to the cutting stem. A distal cutting element is carried by the cutting stem and is rotatable with (Continued)

the proximal cutting element relative to the housing. The distal cutting element includes at least one cutting blade.

11 Claims, 8 Drawing Sheets

(56) References Cited

U.S. PATENT DOCUMENTS

| | | | |
|---|---|---|---|
| 2008/0154296 A1* | 6/2008 | Taylor | A61B 1/32 606/190 |
| 2009/0018565 A1* | 1/2009 | To | A61B 17/320758 606/159 |
| 2012/0109171 A1* | 5/2012 | Zeroni | A61B 17/320758 606/159 |
| 2015/0209066 A1* | 7/2015 | Dahm | A61M 25/0136 606/159 |
| 2020/0129202 A1* | 4/2020 | Schoenle | A61B 17/320783 |

* cited by examiner

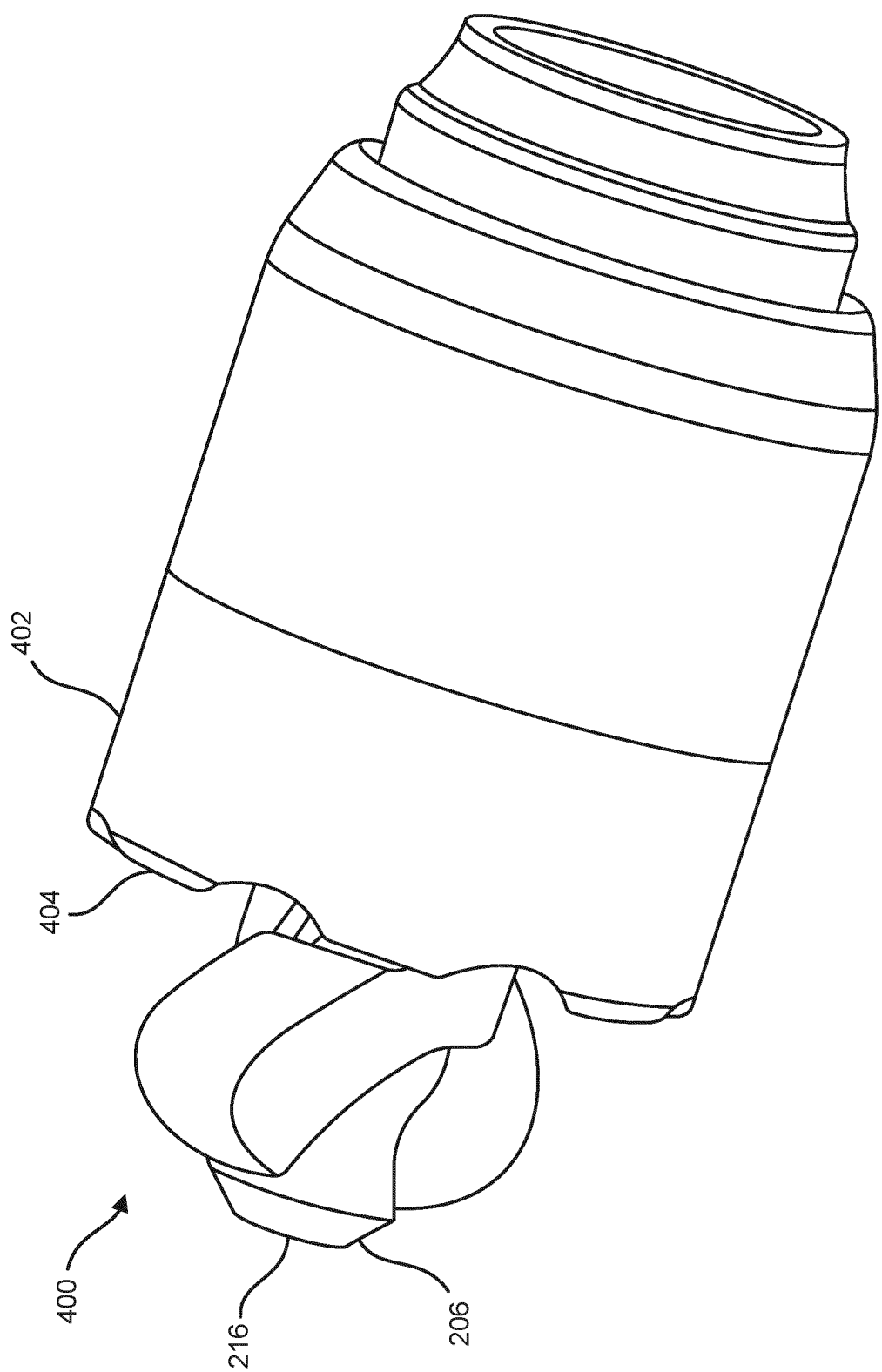

ATHERECTOMY DEVICES INCLUDING A PLURALITY OF DISTAL CUTTING FEATURES

CROSS REFERENCE TO RELATED APPLICATIONS

This application is the U.S. National Phase application under 35 U.S.C. § 371 of International Application No. PCT/EP2020/066184 filed Jun. 11, 2020, which claims the benefit of U.S. Provisional Patent Application No. 62/863,061 filed Jun. 18, 2019. These applications are hereby incorporated by reference herein.

FIELD OF THE DISCLOSURE

The devices and methods described herein generally relate to treatment of occluded body lumens, such as the removal of occlusive material from a blood vessel or other body parts.

BACKGROUND

Peripheral and interventional cardiology is a medical specialty that relates to treatment of various forms of cardiovascular disease, including coronary artery disease and peripheral vascular disease. Coronary artery disease and peripheral vascular disease can arise due to the narrowing of the arteries by atherosclerosis (also called arteriosclerosis). Coronary artery disease generally affects arteries of the heart-arteries that carry blood to cardiac muscles and surrounding tissue. Peripheral vascular disease refers to various diseases of the vascular system outside the heart and brain, which carries blood, for example, to the legs.

Atherosclerosis commonly affects the medium and large arteries, and may occur when fat, cholesterol, and other substances build up on the walls of arteries and form fleshy or hard/calcified structures called plaques/lesions. As plaque forms within an arterial wall, the artery may narrow and become less flexible, which may make it more difficult for blood to flow therethrough. In the peripheral arteries, the plaque is typically not localized, but can extend in length along the axis of the artery for as much as 10 mm or more (in some instance up to 400 mm or more).

Pieces of plaque can break off and move through the affected artery to smaller blood vessels, which may in some instances block them and may result in tissue damage or tissue death (embolization). In some cases, the atherosclerotic plaque may be associated with a weakening of the wall of the affected artery, which can lead to an aneurysm. Minimally invasive surgeries may be performed to remove plaque from arteries in an effort to alleviate or help prevent the complications of atherosclerosis.

A number of interventional surgical methodologies may be used to treat atherosclerosis. In balloon angioplasty, for example, a physician may advance a collapsed, intravascular balloon catheter into a narrowed artery, and may inflate the balloon to macerate and/or displace plaque against the vessel wall. A successful angioplasty may help reopen the artery and allow for improved blood flow. Often, balloon angioplasty is performed in conjunction with the placement of a stent or scaffold structure within the artery to help minimize re-narrowing of the artery. Balloon angioplasty, however, can stretch the artery and induce scar tissue formation, while the placement of a stent can cut arterial tissue and also induce scar tissue formation. Scar tissue formation may lead to restenosis of the artery. In some instances, balloon angioplasty can also rip the vessel wall.

Atherectomy is another treatment methodology for atherosclerosis, and involves the use of an intravascular device to mechanically remove (that is, debulk) plaque from the wall of the artery. Atherectomy devices may allow for the removal of plaque from the wall of an artery, reducing the risk of stretching, cutting, or dissecting the arterial wall and causing tissue damage that leads to restenosis. In some instances, atherectomy may be used to treat restenosis by removing scar tissue.

Unfortunately, some atherectomy devices suffer from structural and performance limitations. For example, the cutting elements or assemblies of some atherectomy devices cannot adequately treat total occlusions. Accordingly, it is desirable to provide improved atherectomy devices and methods.

SUMMARY

The present disclosure presents an atherectomy device including a handle configured to be manipulated by a user. The device further includes a catheter comprising an outer sheath and a drive shaft carried within and rotatable relative to the outer sheath. A cutter assembly is coupled to and extends distally relative to the outer sheath. The cutter assembly includes a housing coupled to and extending distally from the outer sheath. A proximal cutting element is rotatably carried by the housing, and the proximal cutting element is coupled to and extends distally from the drive shaft. The proximal cutting element includes a cutting stem having at least one cutting feature and at least one cutting blade coupled to the cutting stem. A distal cutting element is carried by the cutting stem and is rotatable with the proximal cutting element relative to the housing. The distal cutting element includes at least one cutting blade.

The device according to the previous paragraph, wherein the cutting stem comprises a leading edge, and the at least one cutting feature extends proximally from the leading edge.

The device according to any of the previous paragraphs, wherein the proximal cutting element is rotatable about a rotation axis relative to the housing, and the at least one cutting feature extends in a direction substantially parallel to the rotation axis.

The device according to any of the previous paragraphs, wherein the cutting stem comprises a plurality of cutting features.

The device according to any of the previous paragraphs, wherein the distal cutting element includes a plurality of cutting blades, and the at least one cutting feature is disposed between the plurality of cutting blades.

The device according to any of the previous paragraphs, wherein the housing includes a distal end portion having at least one cutting blade.

The present disclosure also presents an atherectomy device including a handle configured to be manipulated by a user. The device includes a catheter having an outer sheath and a drive shaft carried within and rotatable relative to the outer sheath. A cutter assembly is coupled to and extends distally relative to the outer sheath. The cutter assembly includes a housing coupled to and extending distally from the outer sheath. A cutting element is rotatably carried by the housing, and the cutting element is coupled to and extends distally from the drive shaft. The cutting element comprises a cutting stem having at least one cutting channel and at least one cutting blade coupled to the cutting stem.

The device according to the previous paragraph, wherein the cutting stem comprises a leading edge, and the at least one cutting channel extends proximally from the leading edge.

The device according to any of the previous paragraphs, wherein the cutting element is rotatable about a rotation axis relative to the housing, and the at least one cutting channel extends in a direction substantially parallel to the rotation axis.

The device according to any of the previous paragraphs, wherein the cutting stem comprises a plurality of cutting channels.

The device according to any of the previous paragraphs, wherein the cutting element is a proximal cutting element, and further comprising a distal cutting element carried by the cutting stem and being rotatable with the proximal cutting element relative to the housing, the distal cutting element including at least one cutting blade.

The device according to any of the previous paragraphs, wherein the distal cutting element includes a plurality of cutting blades, and the at least one cutting channel is disposed between the plurality of cutting blades.

The device according to any of the previous paragraphs, wherein the housing includes a distal end portion having at least one cutting blade.

The device according to any of the previous paragraphs, wherein the cutting stem includes an inner lumen configured to receive a guidewire.

The present disclosure also presents an atherectomy device including a handle configured to be manipulated by a user. The device further includes a catheter comprising an outer sheath and a drive shaft carried within and rotatable relative to the outer sheath. A cutter assembly is coupled to and extends distally relative to the outer sheath. The cutter assembly includes a housing coupled to and extending distally from the outer sheath. The housing comprises a distal end portion having at least one cutting blade. A cutting element is rotatably carried by the housing. The cutting element is coupled to and extends distally from the drive shaft, and the cutting element comprises at least one cutting blade.

The device according to the previous paragraph, wherein the distal end portion includes a leading edge, and the at least one cutting blade is disposed at the leading edge.

The device according to any of the previous paragraphs, wherein the cutting element is at least partially disposed proximally relative to the at least one cutting blade of the housing.

The device according to any of the previous paragraphs, wherein the outer sheath and the distal end portion of the housing are rotatably coupled to the handle.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 4 is a perspective view of a distal portion of an atherectomy device according to an embodiment of the present disclosure . . . .

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
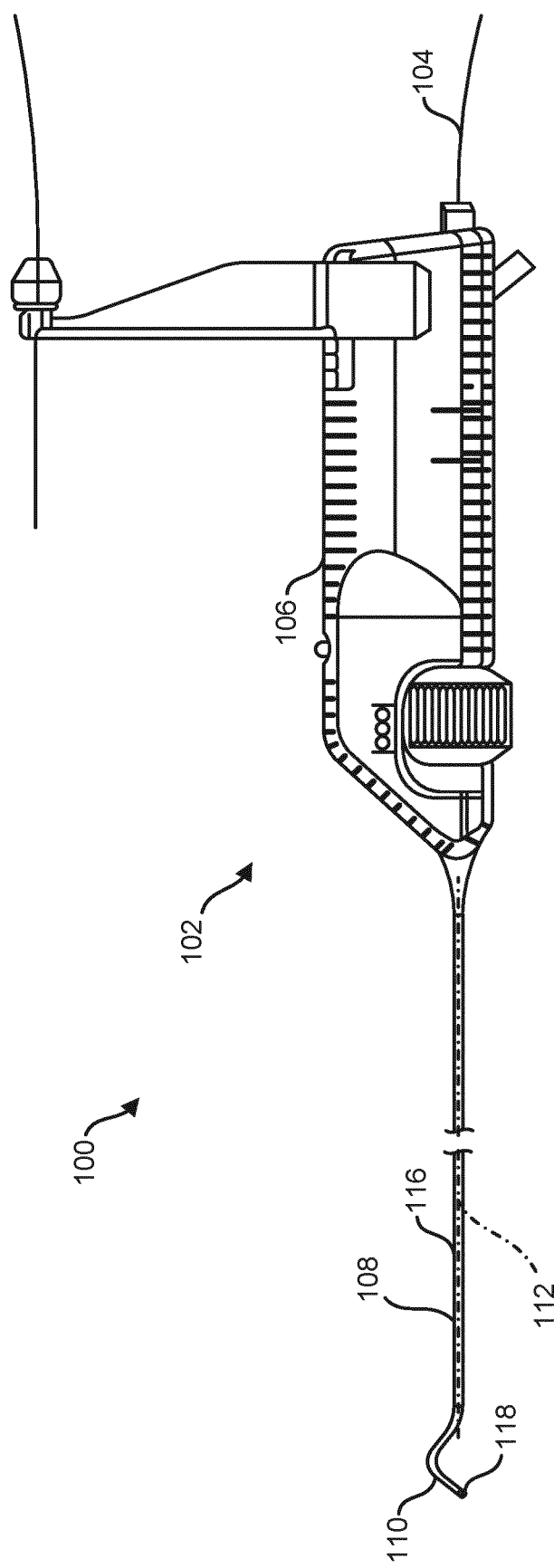
FIG. 1 is a side view of an atherectomy system according to an embodiment of the present disclosure.

The present disclosure relates generally to devices, systems, and methods for mechanical atherectomy. Referring to FIG. 1, there is shown an exemplary embodiment of the atherectomy systems described here. The atherectomy system 100 includes an intravascular atherectomy device 102 and a guidewire 104 over which the atherectomy device 102 may be deployed. In some embodiments, the guidewire 104 is silicon-coated or non-coated (bare), or otherwise free of a PTFE coating. Atherectomy systems according to some embodiments of the present disclosure comprise a guidewire 104 that includes a PTFE coating, or atherectomy systems according to some embodiments of the present disclosure lack a guidewire.

With continued reference to FIG. 1, the atherectomy device 102 generally includes a handle 106 and a catheter 108. The handle 106 is configured to be grasped and manipulated by a user (for example, a medical professional) during an atherectomy procedure. The catheter 108 is coupled to and extends distally relative to the handle 106. The catheter 108 is configured to be positioned in the vasculature of a subject (for example, a patient) during an atherectomy procedure to facilitate removal of occlusive material (for example, plaque) therefrom. In some embodiments and as illustrated, a distal portion 110 of the catheter 108 has a curved shape or configuration. In some embodiments, the distal portion 110 of the catheter 108 normally has a curved configuration ("normally" being understood as the catheter 108 not being subjected to any external contact forces due to, for example, contact with blood vessel walls) and may be deflected to other configurations. In other embodiments, the distal portion 110 of the catheter 108 normally has a straight shape or configuration and may be deflected to other configurations. In some embodiments, the catheter 108 is selectively rotatable about a catheter rotation axis 112 relative to the handle 106 to facilitate appropriately positioning and/or "sweeping" the distal portion 110 of the catheter 108 during an atherectomy procedure. In some embodiments and as illustrated, the handle 106 carries a rotatable knob 114 or dial for selectively rotating the catheter 108 relative to the handle 106. The catheter 108 includes an outer sheath 116, and the outer sheath 116 couples to a cutter assembly 118 that extends distally therefrom. The cutter assembly 118 is described in further detail below.

Figure 2A:
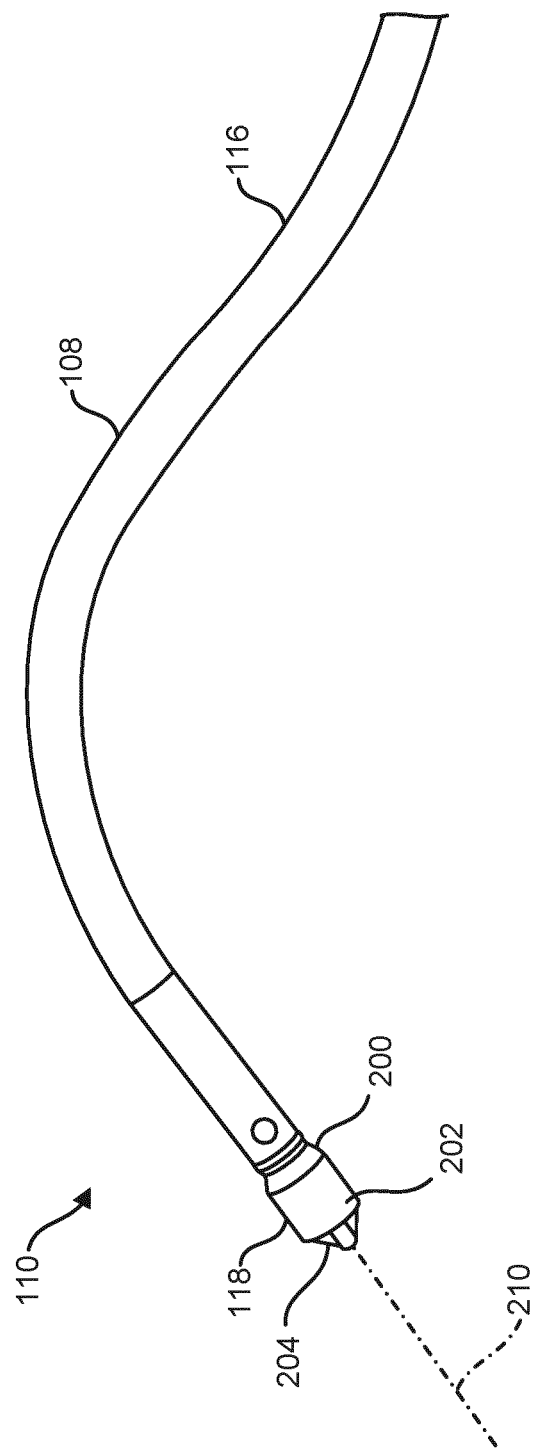
FIG. 2A is a detail side view of a distal portion of the atherectomy system of FIG. 1.
Figure 2B:
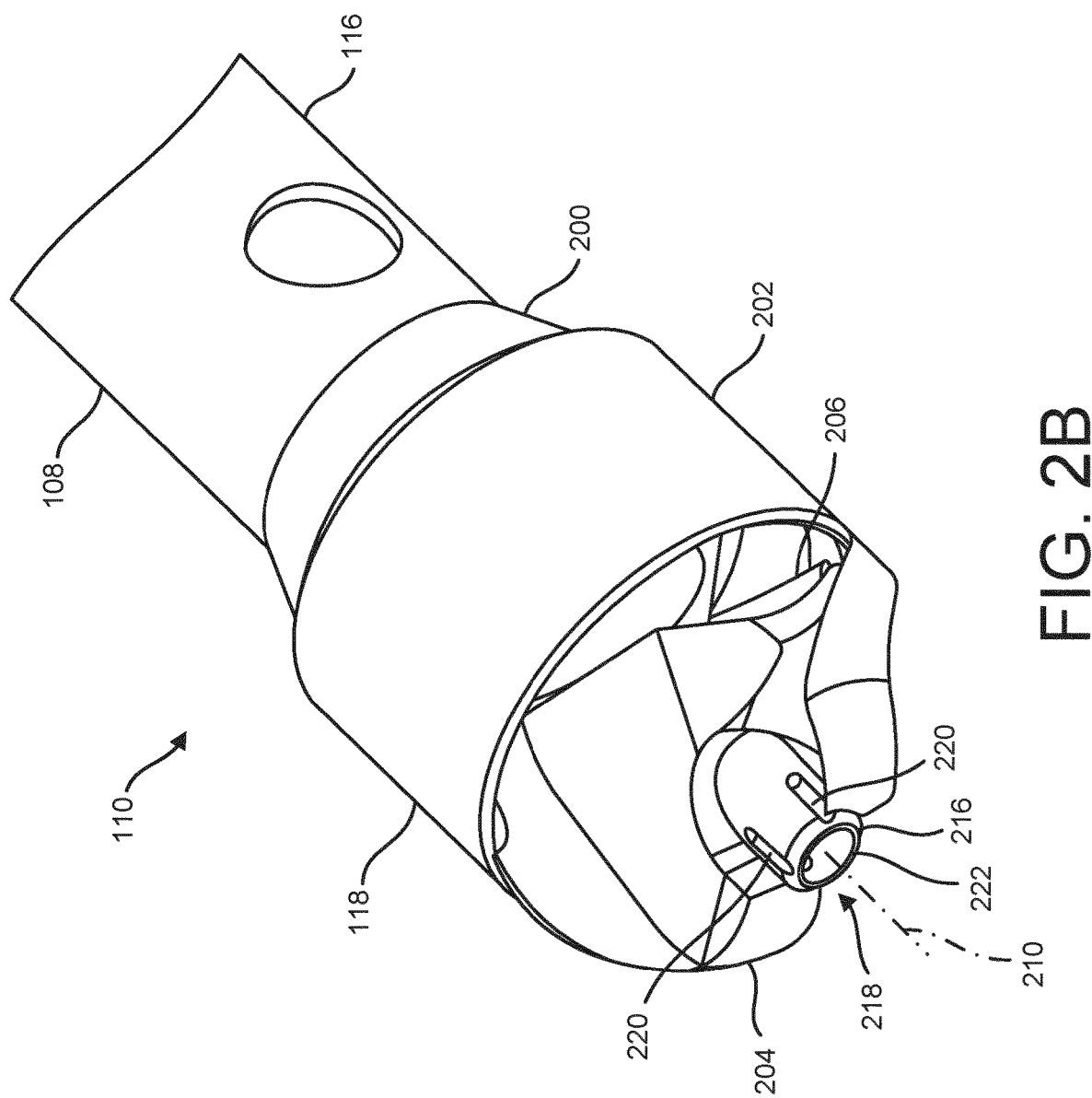
FIG. 2B is a detail perspective view of the distal portion of the atherectomy system of FIG. 1.
Figure 2C:
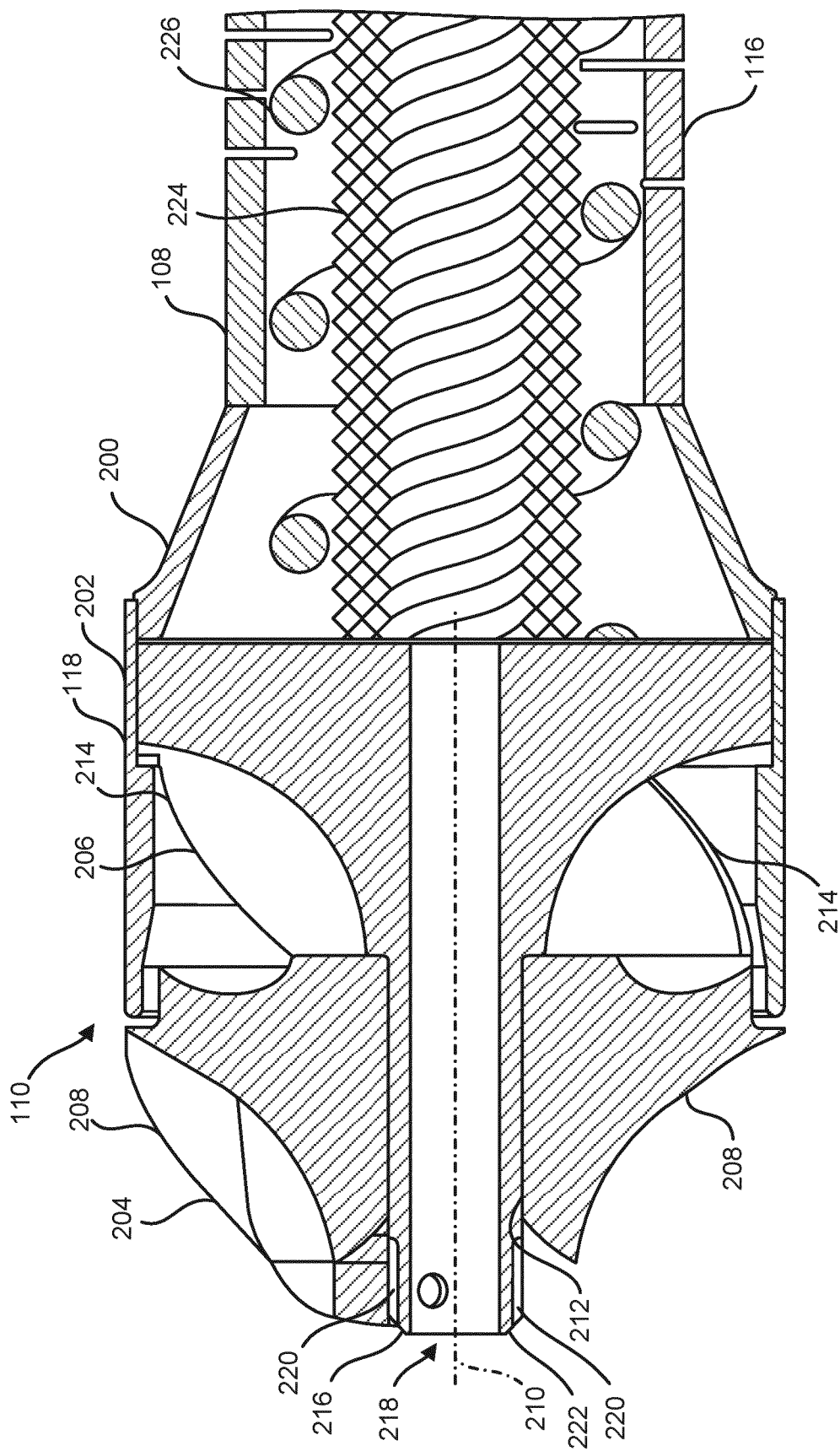
FIG. 2C is a detail transverse sectional view of the distal portion of the atherectomy system of FIG. 2A.
Figure 3A:
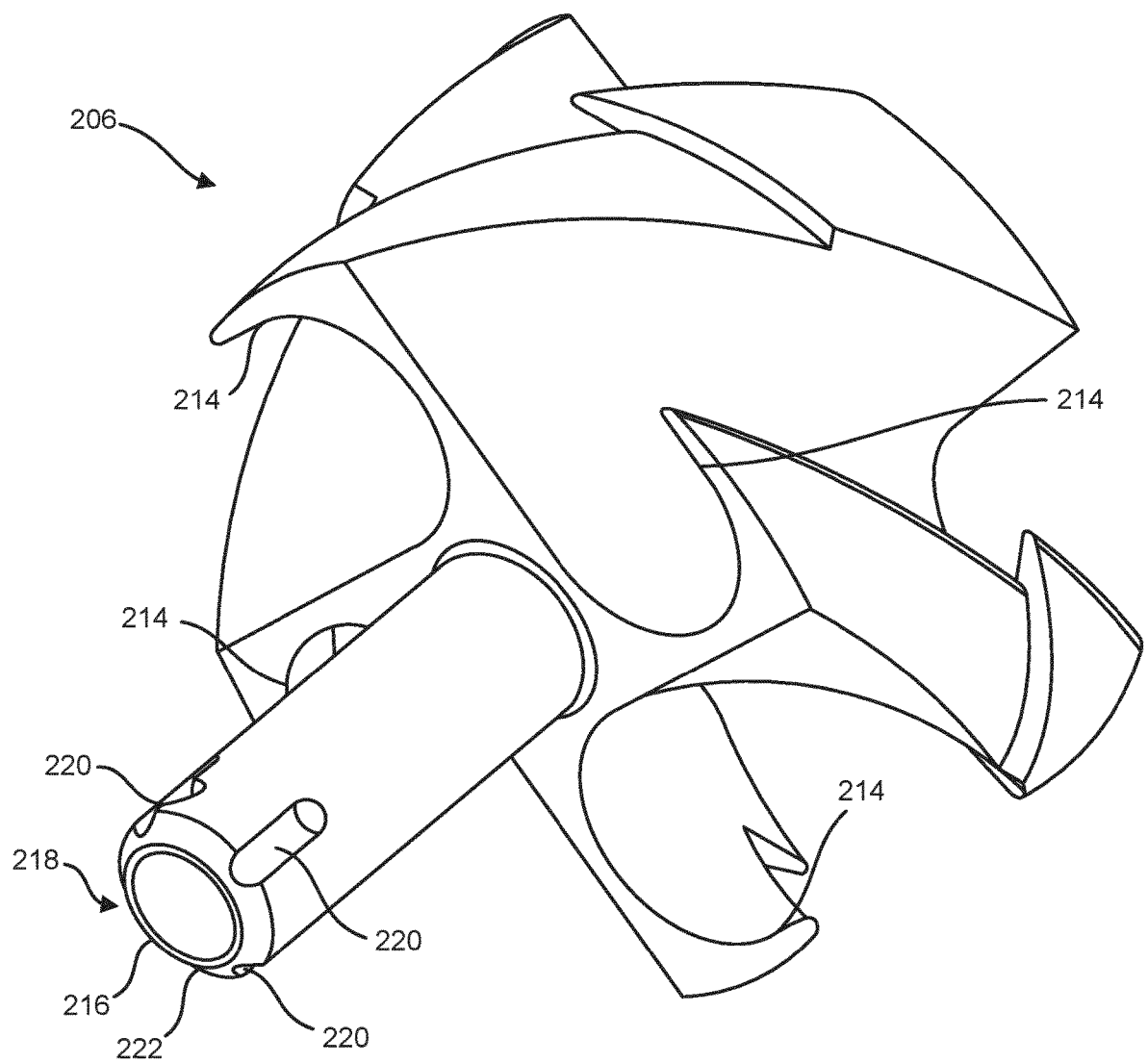
FIG. 3A is a perspective view of a cutting element of the atherectomy system of FIG. 1.
Figure 3B:
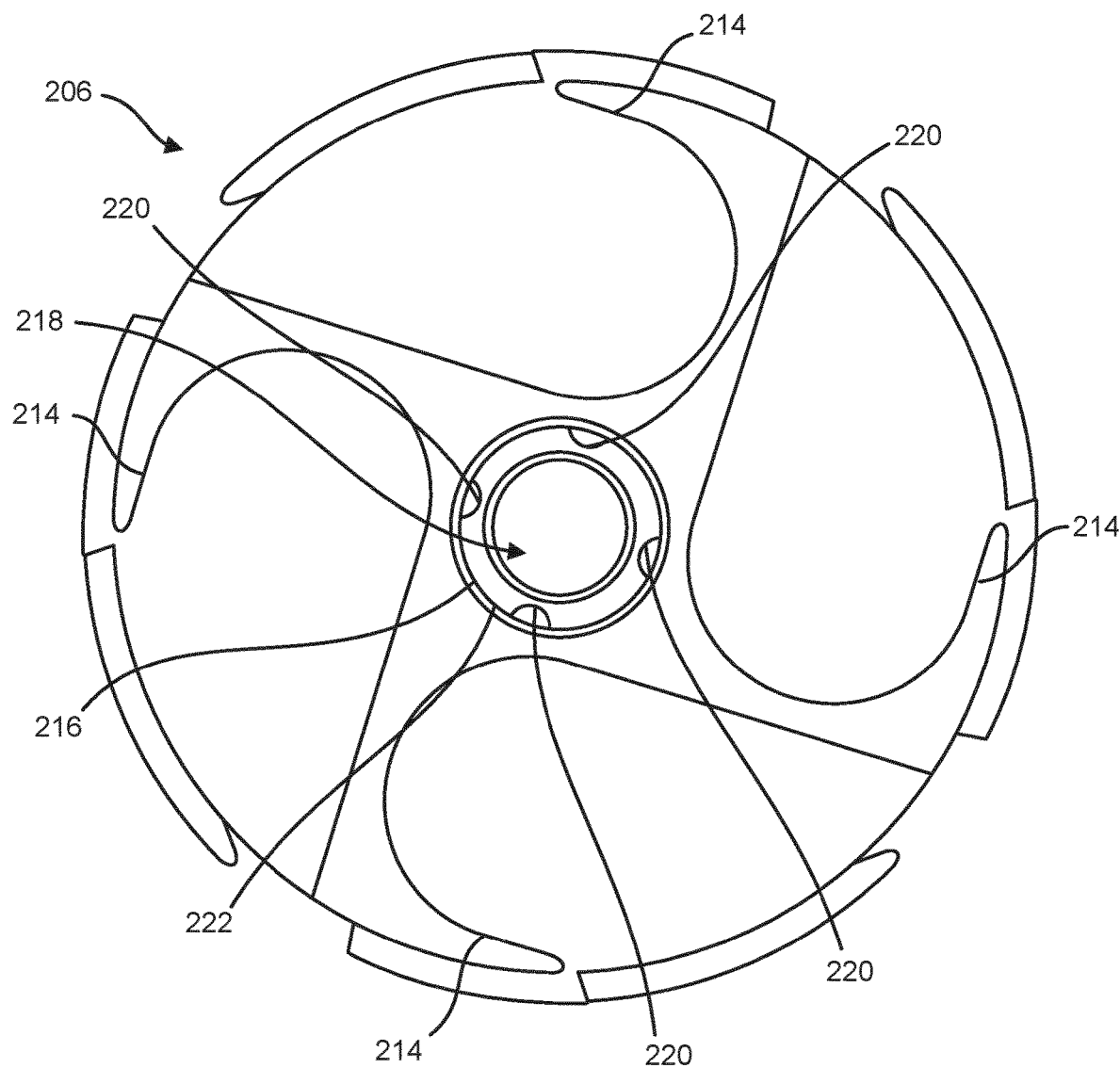
FIG. 3B is a front view of the cutting element of FIG. 3A.

FIGS. 2A-2C illustrate the distal portion 110 of the catheter 108, including, among other components, the outer sheath 116 and the cutter assembly 118. The cutter assembly 118 includes a ferrule 200 that couples to the outer sheath 116 and extends distally therefrom. The cutter assembly 118 further includes a housing 202 that couples to the ferrule 200 and extends distally therefrom. The housing 202 rotatably carries cutting elements. Referring specifically to FIGS. 2B-2C, the housing 202 rotatably carries a first, or distal, cutting element 204 and a second, or proximal, cutting element 206. Rotation of the first cutting element 204 and the second cutting element 206 relative to the housing 202 causes the cutting elements 204, 206 to cut occlusive material and convey the occlusive material into the housing 202 (a process also referred to as "debulking").

Still referring to FIGS. 2B-2C, the first cutting element 204 generally extends distally from the second cutting element 206 and the housing 202. The first cutting element 204 includes one or more cutting flutes or blades 208 that extend distally relative to the housing 202. In some embodiments and as illustrated, the first cutting element 204 includes two cutting blades 208. In some embodiments and as illustrated, the cutting blades 208 extend helically relative to a rotation axis 210 of the first cutting element 204 and the second cutting element 206. The first cutting element 204 includes a central opening 212 (see FIG. 2C) for coupling to the second cutting element 206.

Referring now to FIGS. 2B-2C and 3A-3B, the second cutting element 206 is generally disposed within the housing 202 and, in some embodiments and as illustrated, may be completely disposed within the housing 202 includes one or more cutting flutes or blades 214. In some embodiments, the second cutting element 206 has twice the number of blades as the first cutting element 204. In some embodiments and as illustrated, the second cutting element 206 includes four cutting blades 214. In some embodiments and as illustrated, the cutting blades 214 extend helically relative to the rotation axis 210 of the first cutting element 204 and the second cutting element 206.

The second cutting element 206 is also generally disposed proximally from the first cutting element 204, although the second cutting element 206 includes a cutting shaft or stem 216 that is received in the central opening 212. The cutting stem 216 may couple to the first cutting element 204 in various manners. For example, the cutting stem 216 may couple to the first cutting element 204 via welding. In some embodiments and as illustrated, the cutting stem 216 extends distally relative to the first cutting element 204. The cutting stem 216 includes an inner lumen 218 for receiving a guidewire (shown elsewhere). The cutting stem 216 also includes one or more cutting features 220 that facilitate fragmenting occlusive material into small particles to be captured and removed by the atherectomy system 100. In some embodiments and as illustrated, the cutting stem 216 includes four cutting features 220. In other embodiments, the cutting stem 216 includes a different number of cutting features 220 (for example, one, two, three, five, six, seven, eight, nine, ten, or more cutting features 220). In some embodiments, the cutting features 220 are negative features (for example, channels formed on the surface of the cutting stem 216, as illustrated, or depressions formed on the surface of the cutting stem 216). In some embodiments, the cutting features 220 are positive features (for example, ridges or protrusions extending from the surface of the cutting stem 216). In some embodiments and as illustrated, the cutting features 220 extend proximally from a leading 222 of the cutting stem 216. In some embodiments, the cutting features 220 are disposed apart from the leading 222 and/or do not extend proximally along the stem 216. In some embodiments and as illustrated, the cutting features 220 extend in a direction substantially parallel to the rotation axis 210 (that is, parallel ±10 degrees). In some embodiments, one or more of the cutting features 220 do not extend in a direction substantially parallel to the rotation axis 210 (for example, one or more of the cutting features 220 may extend helically relative to the rotation axis 210). In some embodiments and as illustrated, the cutting features 220 are disposed between the cutting blades 208 of the distal cutting element 204.

Referring specifically to FIG. 2C, the atherectomy device 102 further includes a rotatable drive shaft 224 that couples the first cutting element 204 and the second cutting element 206 to a prime mover (for example, a motor carried by the handle 106—not shown). That is, the prime mover rotates the drive shaft 224, which in turn rotates the first cutting element 204 and the second cutting element 206 to facilitate cutting occlusive material and conveying the occlusive material into the housing 202. In some embodiments, the cutter assembly 118 captures the cut occlusive material from the blood without the use of vacuum aspiration. In other embodiments, vacuum aspiration may assist capture of the cut occlusive material.

With continued reference to FIG. 2C, in some embodiments the atherectomy device 102 also includes an internal conveyor 226 that is coupled to and rotates with the drive shaft 224. As occlusive material is conveyed into the cutter housing 202 by the first cutting element 204 and the second cutting element 206, the conveyor 226 displaces the cut occlusive material proximally through the catheter 108 for discharge outside the subject's body. In some embodiments, this conveyance may occur without the use of vacuum aspiration assistance. In other embodiments, vacuum aspiration may assist conveyance of the cut occlusive material.

Figure 5:
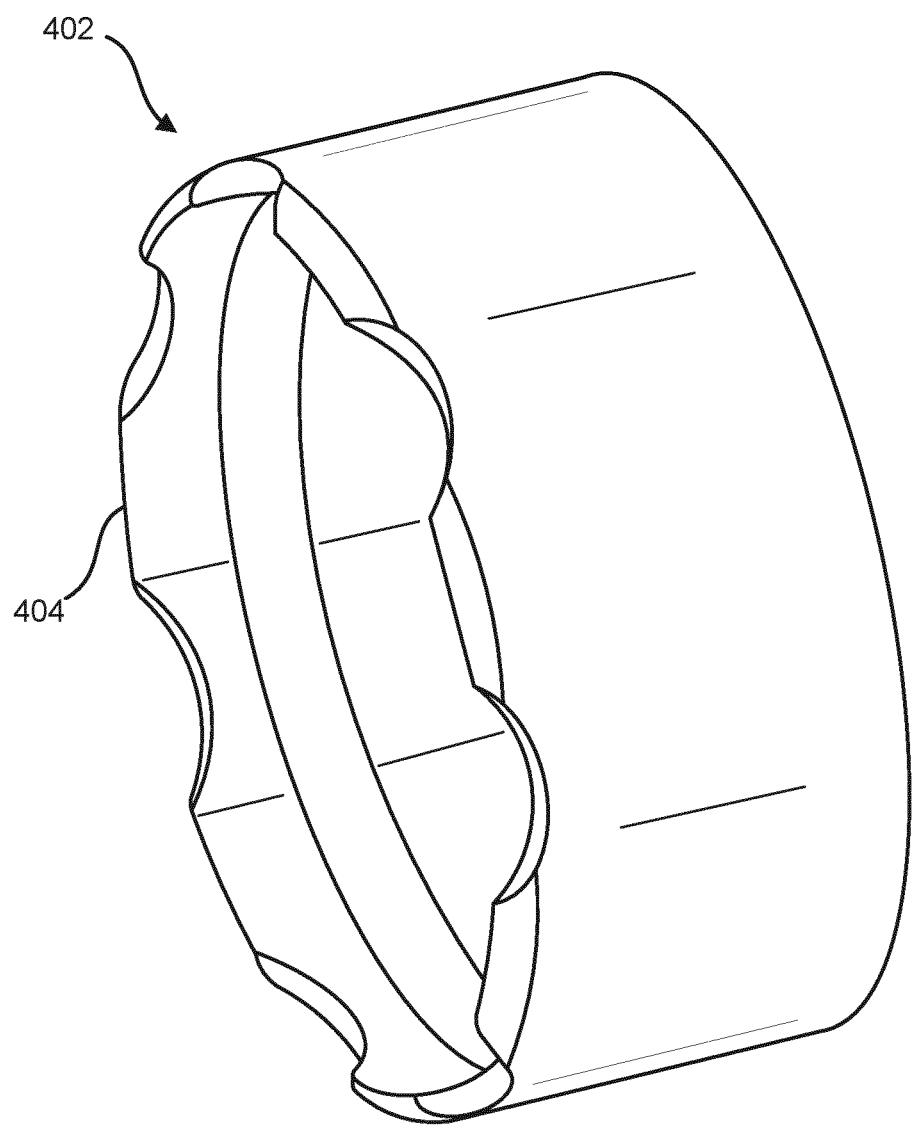
FIG. 5 is a perspective view of a distal end portion of a housing of the distal portion of FIG. 4.

FIG. 4 illustrates a distal portion 400 of a catheter of an atherectomy device according to another exemplary embodiment of the present disclosure. The distal portion 400 of the catheter may be used, for example, in place of the distal portion 110 described above. The distal portion 400 of the catheter may be the same as or similar to the distal portion 110 (for example, the stem 216 of the second cutting element 206 can include one or more cutting features 220 (shown elsewhere, such as any of the cutting features 220 described above)) or different than the distal portion 110 (for example, the stem 216 of the second cutting element 206 may lack any cutting features). The housing of the distal portion 400 includes a distal end portion 402, which is illustrated separately in FIG. 5. The distal end portion 402 includes a leading cutting edge or blade 404. The cutting blade 404 may be used in a passive manner or an active manner. The cutting blade 404 may advantageously provide relatively high luminal gain upon rotation of the outer sheath 116 (for example, via the knob 114 (see FIG. 1, a prime mover (not shown)) and/or deflection of the distal portion 400 of the catheter (for example, as shown in FIG. 1) in the vasculature of a subject. Such a cutting blade 404 may advantageously facilitate effectively debulking a specific type of occlusive material (for example, plaque, more specifically calcified plaque deposits) or various types of occlusive materials. In some embodiments and as illustrated, the cutting blade 404 has a serrated profile. In other embodiments, the cutting blade 404 may have a non-serrated profile.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An atherectomy device, comprising:
    a handle configured to be manipulated by a user;
    a catheter comprising an outer sheath and a drive shaft carried within and rotatable relative to the outer sheath; and
    a cutter assembly coupled to and extending distally relative to the outer sheath, the cutter assembly comprising:
        a housing coupled to and extending distally from the outer sheath;
        a proximal cutting element rotatably carried by the housing, the proximal cutting element being coupled to and extending distally from the drive shaft, the proximal cutting element comprising a cutting stem having at least one cutting feature and at least one cutting blade coupled to the cutting stem; and
        a distal cutting element carried by the cutting stem and being rotatable with the proximal cutting element relative to the housing, wherein the distal cutting element includes a plurality of cutting blades, and the at least one cutting feature is disposed between the plurality of cutting blades.

2. The atherectomy device of claim 1, wherein the cutting stem comprises a leading edge, and the at least one cutting feature extends proximally from the leading edge.

3. The atherectomy device of claim 1, wherein the proximal cutting element is rotatable about a rotation axis relative to the housing, and the at least one cutting feature extends in a direction substantially parallel to the rotation axis.

4. The atherectomy device of claim 1, wherein the cutting stem comprises a plurality of cutting features.

5. The atherectomy device of claim 1, wherein the housing includes a distal end portion having at least one cutting blade.

6. An atherectomy device, comprising:
a handle configured to be manipulated by a user;
a catheter comprising an outer sheath and a drive shaft carried within and rotatable relative to the outer sheath; and
a cutter assembly coupled to and extending distally relative to the outer sheath, the cutter assembly comprising:
a housing coupled to and extending distally from the outer sheath;
a proximal cutting element rotatably carried by the housing, the proximal cutting element being coupled to and extending distally from the drive shaft, the proximal cutting element comprising a cutting stem having at least one cutting channel and at least one cutting blade coupled to the cutting stem; and
a distal cutting element carried by the cutting stem and being rotatable with the proximal cutting element relative to the housing, the distal cutting element including a plurality of cutting blades, and the at least one cutting channel is disposed between the plurality of cutting blades.

7. The atherectomy device of claim 6, wherein the cutting stem comprises a leading edge, and the at least one cutting channel extends proximally from the leading edge.

8. The atherectomy device of claim 6, wherein the cutting element is rotatable about a rotation axis relative to the housing, and the at least one cutting channel extends in a direction substantially parallel to the rotation axis.

9. The atherectomy device of claim 6, wherein the cutting stem comprises a plurality of cutting channels.

10. The atherectomy device of claim 6, wherein the housing includes a distal end portion having at least one cutting blade.

11. The atherectomy device of claim 6, wherein the cutting stem includes an inner lumen configured to receive a guidewire.

* * * * *